United States Patent [19]

LeVeen et al.

[11] 4,367,739

[45] Jan. 11, 1983

[54] SYRINGE

[76] Inventors: Harry H. LeVeen, 321 Confederate Cir., Charleston, S.C. 29407; Eric G. LeVeen, 3-3 Woodlike Rd., Albany, N.Y. 12203; Robert F. LeVeen, 312 Lombard St., Philadelphia, Pa. 19147

[21] Appl. No.: 255,352

[22] Filed: Apr. 20, 1981

[51] Int. Cl.³ .................. A61M 1/00

[52] U.S. Cl. .................. 128/236; 128/218 PA

[58] Field of Search .................. 128/236, 234, 215, 216, 128/218 R, 218 P, 218 PA, 218 F, 220, 218 C; 222/48, 46, 44, 41, 39, 390

[56] References Cited

U.S. PATENT DOCUMENTS 605,386 6/1898 Brown .................. 128/236

4,189,065 2/1980 Herold .................. 128/236

*Primary Examiner*—John D. Yasko

*Attorney, Agent, or Firm*—Brooks, Haidt, Haffner & Delahunty

[57] ABSTRACT

A syringe comprising a cylindrical barrel with a wall at one end with a nozzle and with a threaded actuating rod extending from its other end, the rod carrying a piston in fluid tight engagement with the inner wall of the barrel. The rod also carries a collar with threads which mate with the rod threads, and the collar has slots which engage projections on the barrel and prevent movement of the collar relative to the barrel but which permit the collar to be disengaged readily from the barrel. A manually engageable knob is rotatably mounted on the rod at its end remote from the piston and is interconnected with the rod by a compressible, spiral spring. A ratchet wheel is mounted on the rod so as to rotate therewith and is adjacent the knob. The knob carries a spring biased pawl in the form of a tooth which is engageable with the ratchet wheel teeth. As the pressure on the fluid in the barrel is increased, the spring is compressed and the knob rotates with respect to the rod causing the pawl to assume a position dependent on the pressure.

7 Claims, 4 Drawing Figures

2 3 21 23 8 14 12 1 3 2 5 4 9 10 11 13 6 2 3

SYRINGE

This invention relates to a syringe for precisely dispensing fluids against relatively high fluid resistance and particularly, to a syringe of such type which has means for indicating the pressure applied to the fluid being dispensed.

Related applications are co-pending application Ser. No. 61,642, filed July 30, 1979, in the names of two of the inventors named herein and entitled "Syringe" and co-pending application Ser. No. 6/255,353, filed concurrently herewith, in the names of the inventors named herein and entitled "Syringe".

Syringes are well known in the medical art and are commonly used to supply a fluid to a vein or body cavity or to a device, such as an arterial embolectomy catheter or a tracheal balloon. In some such applications, it is desirable to be able to know the pressure which is being applied to the fluid by the syringe.

Such syringes usually include a hollow cylinder or barrel with an opening or nozzle at one end and a piston or plunger therein which is slidably reciprocable within the cylinder by means of a manually engageable rod or shaft extending from the opposite end of the cylinder. The piston has fluid tight engagement with the inner wall of the cylinder so that as the piston is moved toward the nozzle, fluid can be ejected from the nozzle. The nozzle can be connected to a needle, a catheter or other device.

Said co-pending application Ser. No. 61,642 describes a syringe which overcomes problems of prior art syringes in which the piston and its actuator are manually reciprocated. The syringe comprises a hollow cylinder with a wall at one end having an opening through which the fluid is transported. The opposite end of the hollow cylinder is open and receives a piston rotatably mounted on one end of a threaded rod having a knurled knob at its opposite end. The rod carries a collar having a threaded portion which mates with the thread on the rod. The opposite end of the cylinder has a pair of projections which interfit with a portion of the collar so that after the cylinder is partially filled with the fluid to be transported and the piston is in the cylinder, the collar can be rotated on the rod until it engages the projections which prevents further movement of the collar axially of the cylinder. When the rod is thereafter rotated by means of the knob, the piston moves axially of the cylinder to dispense the fluid through the opening in the end wall thereof. The present invention will be described as applied to a syringe of the type disclosed in said application.

One object of the invention is to provide a self-contained syringe which permits the delivery of fluid under pressure through the syringe opening and which includes means thereon which indicates the pressure being applied to the fluid by the piston of the syringe.

Another object of the invention is to provide such a syringe which may be quickly and easily filled with the fluid to be transported through the syringe opening.

It also is an object of the invention to provide such a syringe which is of such simple construction and economical manufacture that it can be dispensed in a sterile package and be disposed of after use.

In accordance with the preferred embodiment of the invention, the syringe comprises a hollow cylinder with a wall at one end having an opening through which the fluid passes. The opposite end of the hollow cylinder is open and receives a piston rotatably mounted on one end of a threaded rod and having a knurled knob rotatably mounted at its opposite end. The knob is connected to the rod by a spring, and as the force applied to the knob is increased to increase the pressure on the fluid in the cylinder, the knob rotates with respect to the rod and increases the spring tension. A ratchet wheel is secured in fixed relation to the rod adjacent the knob and an indicator arm mounted for movement with the knob engages the teeth of the ratchet wheel. Accordingly, the position of the indicator arm with respect to the teeth indicates the force being applied to rotate the rod and hence, the pressure applied to the fluid in the cylinder. As in said application Ser. No. 61,642, the rod carries a collar having a threaded portion which mates with the threads on the rod. The opposite end of the cylinder has a pair of projections which interfit with a portion of the collar so that after the cylinder is partially filled with the fluid to be expelled therefrom and the piston is inserted in the cylinder, the collar can be rotated until it engages the projections, at which time further movement of the collar axially of the cylinder is prevented. When the rod is thereafter rotated by means of the knob, the piston moves axially of the cylinder to expel the fluid through the opening in the end wall thereof.

Other objects and advantages of the present invention will be apparent from the following detailed description of the presently preferred embodiments thereof, which description should be considered in conjunction with the accompanying drawing in which.

Figure 1:
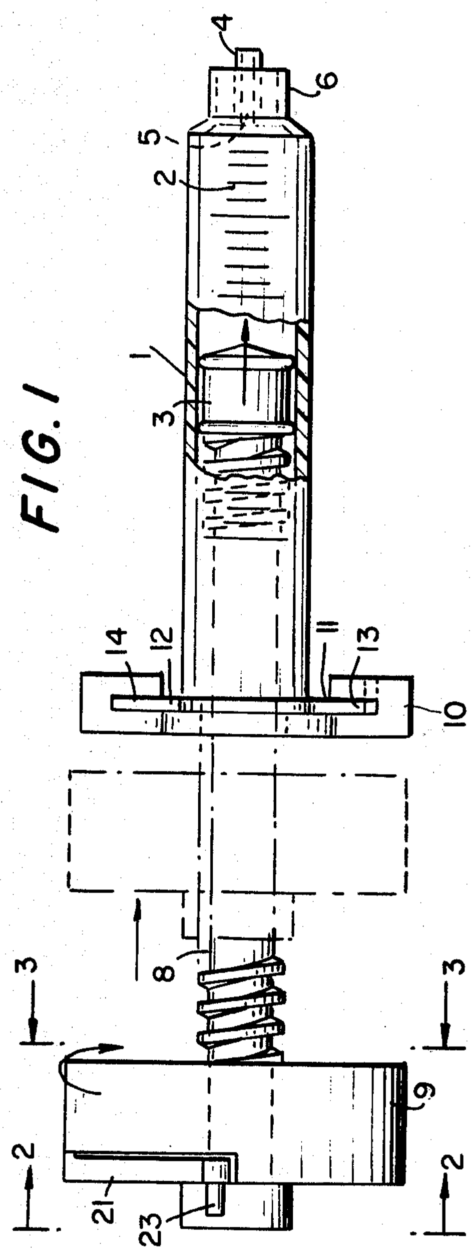
FIG. 1 is a side view, partly in section, of the preferred embodiment of the invention.
Figure 4:
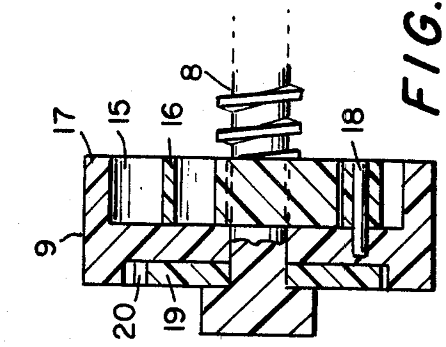
FIG. 4 is a cross-sectional view of a portion of the preferred embodiment shown in FIG. 1 and is taken along the line 4—4 indicated in FIG. 3.

The syringe illustrated in the figures of the drawing comprises a cylinder 1 made of a transparent or semi-transparent plastic material permitting visual observation of the contents therein. Graduations 2 are provided in the outer surface of the cylinder 1 to permit measurement of the movement of the piston 3 and hence, of the volume of fluid transported through the nozzle 4 having an opening 5 and surrounded by a sleeve 6 having internal threads for attaching other devices, such as a catheter, valve or tubular device, to the syringe. The piston 3 fits snugly within the bore of the cylinder 1 to provide a fluid tight engagement with the interior wall thereof and is made of a resilient material, such as neoprene rubber. The piston 3 is formed internally so that it snaps over an enlarged portion at the end of a threaded rod 8, as described in said application Ser. No. 61,642.

The rod 8 extends from the end of the cylinder 1 opposite the end thereof having the nozzle 4 and the opening 5 and has a knurled knob 9 at the end thereof opposite the end of the rod 8 which carries the piston 3. The knob 9 is rotatably mounted on the rod 8, and preferably, the rod 8 and the knob 9 are molded from a plastic material, such as an acetal polymer.

The rod 8 carries a collar 10, which may be made of the same material as the rod 8, and which has a threaded bore, the threads of which mate with the threads on the rod 8. Preferably, the fit of the threads is such that when the collar 10 is disengaged from projections 11 and 12 on the cylinder 1, the collar 10 can be spun to permit rapid adjustment of the collar 10 in the axial direction of the rod 8.

The projections 11 and 12 on the cylinder 1 and slots 13 and 14 in the collar 10 form co-operating and interengaging means for releasably securing the collar 10 to the cylinder 1. The diameter of the projections 11 and 12 preferably is slightly larger than the internal diameter of the slots 13 and 14, or the axial dimensions of the slots 13 and 14 preferably are slightly less than the axial dimensions of the projections 11 and 12, or both, so that when the projections 11 and 12 are in the slots 13 and 14 the friction therebetween will prevent rotation of the collar 10 with rotation of the rod 8. In addition, the end of the slot 13 can be blocked by a pin 15 (FIG. 1), so that rotation of the collar 10 within the slots 13 and 14 is limited in one direction. However, the collar 10 and the projections 11 and 12 are shaped as indicated in the drawing, and the dimensions of the slots 13 and 14 and the projections 11 and 12 are such, that the collar 10 can be disengaged from the cylinder 1 by manually rotating the collar 10 by one-quarter of a turn with repect to the cylinder 1. When so released, the rod 8 and the piston 3 can be inserted in, or removed from, the cylinder 1 by movement of the rod 8 axially of the cylinder 1 and without rotation of the rod 8.

Figure 3:
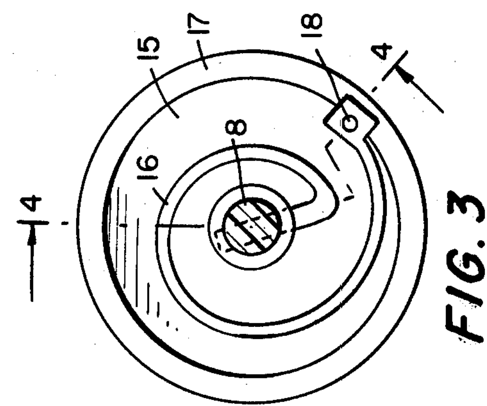
FIG. 3 is a view, partly in cross-section, taken at one side of the syringe knob shown in FIG. 1 and is taken along the line 3—3 indicated in FIG. 1.
Figure 2:
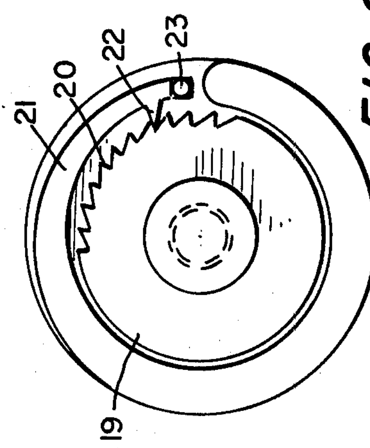
FIG. 2 is an end view of the preferred embodiment, shown in FIG. 1.

The knob 9 has a cavity 15 (FIG. 3) which receives a spiral spring 16, one end of which is received in an aperture in the rod 8 and the other end of which is secured to the rim 17 of the knob 9 by a pin 18. A ratchet wheel 19, having peripheral teeth 20, is secured to the rod 8 so as to rotate therewith. The knob 9 carries pawl means in the form of a resilient arm 21 with a tooth 22 which can fit between the teeth 20. However, the shapes of the tooth 22 and the teeth 20 are such that while the tooth 22 can ride over the teeth 20 when the knob 9 is rotated clockwise (as seen in FIG. 2) rotation of the knob 9 counterclockwise causes rotation of the wheel 19 in the same direction. The arm 20 has a projection 23 (FIG. 1) by which the tooth 22 can be manually disengaged from the teeth 20. Preferably, the arm 21 is integral with the knob 9, and the ratchet wheel 19 and the spring 16 are made of the same material as the knob 9 and the rod 8.

Of course, the positions of the pawl means and the ratchet teeth 20 could be interchanged, i.e. the teeth 20 can be carried by the knob 9 and the arm 21 and the tooth 22 can be carried by the wheel 19 or extend from the rod 8.

In use, the piston 3 is withdrawn in the cylinder 1, by disengaging the projections 11 and 12 from the collar 10 and pulling the rod 8 away from the nozzle 4, to draw the desired fluid into the cylinder 1. The collar 10 is then rotated to carry it down the rod 8 until the projections 11 and 12 are in the slots 13 and 14.

In one method of using the syringe of the invention, the tooth 22 is released from the teeth 20 by manually engaging the projection 23 and moving it radially of the knob 9 which permits the knob to rotate counterclockwise on the rod 8 as viewed in FIG. 2, under the action of the spring 16. When the projection 23 is then released, the tooth 22 will enter into the space between a pair of teeth near the left end of the row of teeth 20 shown in FIG. 2. Thereafter, when the knob 9 is rotated clockwise, as viewed in FIG. 2, the rotating force applied to the knob 9 will be transmitted to the rod 8 by way of the spring 16. If the resistance of the spring 16 to coiling compression is greater than the force required to rotate the rod 8, the rod 8 will rotate without causing displacement of the tooth 22 from the position into which it was initially set. However, when the force required to rotate the rod 8 increases, such as by reason of the pressure applied to the fluid in the cylinder 1 by the piston 3, a point will be reached at which the rotating force applied to the knob 9 to cause rotation of the rod 8 is such that the knob 9 will rotate with respect to the rod 8 with accompanying compression of the spring 16. When the knob 9 rotates with respect to the rod 8, the tooth 22 will move clockwise, as viewed in FIG. 2, and the position of the tooth 22 is an indication of the pressure applied to the fluid in the cylinder 1 by the piston 3.

The teeth 20 could be replaced by graduation marks on the wheel 19, the position of the tooth 22, or other indicia, with respect to such marks indicating the pressure applied to the fluid by the piston 3. However, the ratchet wheel teeth 20 are preferred for several reasons. In the first place, when a desired pressure on the fluid is reached, the knob 9 may be released, and the knob 9 will remain in the position reached before release. When it is desired to reduce the pressure, the knob 9 is rotated clockwise, and because of the engagement of the tooth 22 with the teeth 20, the knob 9 has a rigid connection with the rod 8 causing the rod 8 to move with the knob 9.

In the second place, the pressure which has been reached can be detected by listening to, and counting the number of, the "clicks" as the tooth 22 rides over the teeth 20, and it is unnecessary to visually observe the position of the tooth 22.

In the third place, the use of a ratchet wheel 19 permits the use of the syringe in another way. Thus, before or after the cylinder 1 has been filled with fluid to the desired level and the piston 3 has been inserted into the cylinder 1, the rod 8 can be held manually and the knob 9 can be turned clockwise until the tooth 22 occupies the space between a pair of the teeth 20 which represents a pressure immediately below the maximum pressure to be applied. For example, if the tooth 22 is positioned in the space between a pair of teeth 20 which is immediately adjacent the space representing the maximum pressure, thereafter, when the rod 8 is rotated by the knob 9 by way of the spring 16, a single "click" will be heard when the pressure on the fluid reaches the maximum desired pressure. Accordingly, with this method of use, it is not necessary to observe the tooth 22 visually to determine when the maximum pressure has been reached.

Although preferred embodiments of the present invention have been described and illustrated, it will be apparent to those skilled in the art that various modifications can be made without departing from the principles of the invention.

We claim:

1. A manually actuable syringe comprising:

a hollow body with an interior wall, a fluid transport opening at one end thereof and a piston receiving opening at the opposite end thereof;

a piston within said body which has fluid tight engagement with said interior wall, said piston being slidable toward and away from said transport opening;

a manually operable actuating rod extending at one end from said piston receiving opening and slidable within said body, said rod having means engageable with said body for moving said rod toward said transport opening when said rod is rotated and being connected to said piston at one end of said rod;

a manually engageable knob rotatably mounted on said rod at the end thereof opposite from the end thereof which is connected to said piston;

spring means interconnecting said knob with said rod and opposing rotation of said knob with respect to said rod;

means adjacent said knob rotatable with said rod;

means on said knob adjacent said means rotatable with said rod for indicating rotation of said knob relative to said rod and thereby, indicating the pressure applied to fluid within said body of said piston.

2. A syringe as set forth in claim 1 wherein said actuating rod is a threaded rod and further comprising;

a collar mounted on said threaded rod, said collar having a threaded portion mating with the threads on said threaded rod and said collar and said threaded rod being rotatable relative to each other to cause relative movement of said collar and said threaded rod in a direction longitudinally of said rod; and co-operating and interengaging means on said body and said collar for releasably securing said collar to said body and thereby preventing movement of said collar in a direction extending from one end to the other of said body, whereby rotation of said threaded rod causes said piston to move in said direction.

3. A syringe as set forth in claim 2 wherein said spring means is a spiral spring connected at one end to said rod and connected at the opposite end to said knob.

4. A syringe as set forth in claims 1 or 3 wherein said means rotatable with said rod is a ratchet wheel having teeth and wherein said means on said knob is pawl means engageable with the teeth on said ratchet wheel.

5. A syringe as set forth in claim 4 wherein said pawl means comprises a resilient arm secured at one end to said knob and having a tooth at its opposite end, said tooth being receivable between teeth of said ratchet wheel and permitting rotation of said knob in a direction which causes said piston to move toward said transport opening but which prevents rotation of said knob in the opposite direction with respect to said rod.

6. A syringe as set forth in claim 2 wherein said cooperating and interengaging means comprises a pair of spaced projections on said body adjacent said opposite end thereof which extend radially outwardly from said body and which are spaced from each other circumferentially of the body, said projections having a circumferential length less than one-half of the circumference of said body, and said collar has slots therein for receiving said projections, said projections engaging walls of said slots when said collar is adjacent said opposite end and is rotated through a partial turn, and stop means on said collar engageable with at least one of said projections for limiting rotation of said collar.

7. A syringe as set forth in claim 6 wherein said stop means comprises a pin projecting into an end portion of one of said slots.

* * * * *